United States Patent [19]

Pfaffli

[11] 4,123,535

[45] Oct. 31, 1978

[54] PSYCHOSTIMULATING 14-AMINO-14,15-DIHYDROEBURNAME-NINES

[75] Inventor: Paul Pfaffli, Arlesheim, Switzerland

[73] Assignee: Sandoz Ltd., Basel, Switzerland

[21] Appl. No.: 788,510

[22] Filed: Apr. 18, 1977

Related U.S. Application Data

[62] Division of Ser. No. 609,357, Sep. 2, 1975, Pat. No. 4,045,443.

[30] Foreign Application Priority Data

Sep. 6, 1974 [CH] Switzerland ................. 12153/74
Jun. 3, 1975 [CH] Switzerland ................. 7118/75

[51] Int. Cl.$^2$ ............... C07D 519/04; A61K 31/445
[52] U.S. Cl. ........................ 424/256; 260/293.53; 260/293.55
[58] Field of Search ............ 260/293.53, 293.55; 424/256, 267

[56] References Cited

U.S. PATENT DOCUMENTS 3,753,995  8/1973  Martel et al. ............. 260/293.53
3,925,393  12/1975  Heurtaux et al. .......... 424/267

FOREIGN PATENT DOCUMENTS 772,006  8/1971  Belgium ................. 260/293.53
797,328  3/1973  Belgium ................. 260/293.53

OTHER PUBLICATIONS

Cava, M. et al., Chemistry and Industry, pp. 1242-1243, (1963).

Primary Examiner—Henry R. Jiles
Assistant Examiner—Richard A. Schwartz
Attorney, Agent, or Firm—Gerald D. Sharkin; Robert S. Honor; Thomas O. McGovern

[57] ABSTRACT

This invention provides new compounds of formula I,

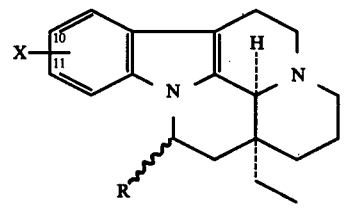

wherein
  X is hydrogen or halogen having an atomic number from 9 to 35 in the 10- or 11-position, and
  R is a radical of the series $OR_1$, $SR_2$, $NR_3R_4$,
wherein
  $R_1$ and $R_2$ are alkyl of 1 to 4 carbon atoms, hydroxyalkyl or aminoalkyl of 2 to 4 carbon atoms, phenyl or phenylalkyl of 7 to 10 carbon atoms in the aggregate thereof, and
  $R_3$ and $R_4$ are, independently, hydrogen, alkyl of 1 to 4 carbon atoms, phenyl or phenylalkyl of 7 to 10 carbon atoms in the aggregate thereof.

useful as psycho-stimulants or vigilance increasing agents.

11 Claims, No Drawings

PSYCHOSTIMULATING 14-AMINO-14,15-DIHYDROEBURNAMENINES

This is a division of application Ser. No. 609,357 filed Sept. 2, 1975 which issued as U.S. Pat. No. 4,045,443 on Sept. 9, 1977.

IMPROVEMENTS IN OR RELATING TO ORGANIC COMPOUNDS

The present invention relates to new organic compounds.

In accordance with the invention there are provided new compounds of formula I,

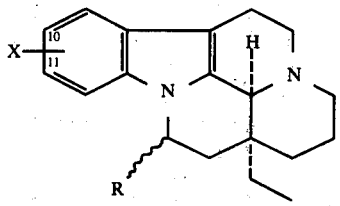

wherein
X is hydrogen or halogen having an atomic number from 9 to 35 in the 10- or 11-position, and
R is a radical of the series $OR_1$, $SR_2$, $NR_3R_4$,
wherein
$R_1$ and $R_2$ are alkyl of 1 to 4 carbon atoms, hydroxyalkyl or aminoalkyl of 2 to 4 carbon atoms, wherein the hydroxy and amino groups are in other than the α-position to the O or S atom, phenyl or phenylalkyl of 7 to 10 carbon atoms in the aggregate thereof, and
$R_3$ and $R_4$ are, independently, hydrogen, alkyl of 1 to 4 carbon atoms, phenyl or phenylalkyl of 7 to 10 carbon atoms in the aggregate thereof.

X especially signifies hydrogen, fluorine or bromine. When X is fluorine, it is preferably in the 10-position; when X is bromine, it is preferably in the 11-position. R preferably signifies $SR_2$.

When $R_1$ or $R_2$ is alkyl of 1 to 4 carbon atoms, then this specially signifies methyl or ethyl, preferably methyl.

When $R_1$ or $R_2$ is hydroxyalkyl of 2 to 4 carbon atoms, then this preferably signifies 2-hydroxyethyl.

When $R_1$ or $R_2$ is aminoalkyl of 2 to 4 carbon atoms, then this preferably signifies 2-aminoethyl.

When $R_1$ or $R_2$ is phenylalkyl of 7 to 10 carbon atoms, then this preferably signifies benzyl or 2-phenylethyl.

$R_1$ especially signifies methyl. $R_2$ especially signifies methyl or 2-hydroxyethyl.

When $R_3$ or $R_4$ is alkyl of 1 to 4 carbon atoms, then this especially signifies methyl or ethyl, preferably methyl.

When $R_3$ or $R_4$ is phenylalkyl of 7 to 10 carbon atoms, then this preferably signifies benzyl or 2-phenylethyl.

In hydroxyalkyl, aminoalkyl or phenylalkyl, the respective hydroxy, amino or phenyl radical is conveniently located at the omega position of the alkyl moiety.

Further, in accordance with the invention a compound of formula I may be obtained by a process comprising
a) reacting a compound of formula II,

HR'   II wherein
R' is an $OR_1$ or $SR_2$ radical wherein
$R_1$ and $R_2$ are as defined above,
with a compound of formula III,

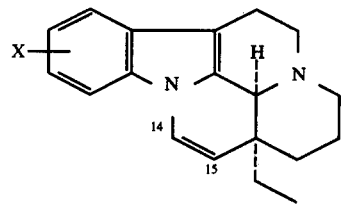

wherein
X is as defined above, to produce a compound of formula Ia,

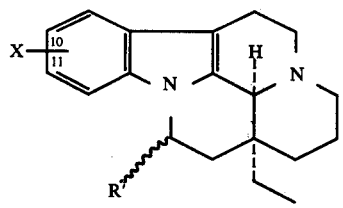

wherein
R' and X are as defined above, or
b) replacing the radical Z by the radical R in a compound of formula IV,

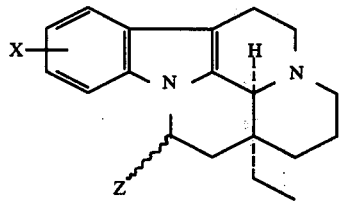

wherein
X is as defined above, and
Z is a radical capable of being exchanged for the radical R.

Processes (a) and (b) may be carried out in accordance with known methods.

Process (a) is an addition reaction. It is effected under acid conditions, conveniently in the absence of water. 1.0 to 2.0 mols of acid, e.g., sulphuric acid or methanesulphonic acid, may, for example, be used, for every mol of the compound III.

The reaction may be effected in an inert solvent, e.g., chloroform, or in an excess of the compound of formula II. The reaction temperature may vary; the reaction is generally conveniently effected at room temperature or preferably at an elevated temperature, e.g., between 40° and 80° C.

Process (b) is a nucleophilic substitution reaction which may, for example, be effected by reacting a compound of formula IV with a compound of formula V,

MR   V wherein
M is hydrogen or an alkali metal, and

R is as defined above.

Z in the compounds of formula IV may, for example, signify halogen, e.g., bromine or chlorine. M in the compounds of formula V may, for example, signify sodium, lithium, potassium or hydrogen.

Compounds of formula IV wherein Z is halogen are hydrogen halide addition products of compounds of formula III. They are unstable. When these compounds are reacted with a compound of formula V or an alkali metal salt thereof it is convenient to use a reaction temperature below −20° C.

An excess of the compound of formula V used may, for example, be employed as solvent, insofar as this is liquid at the reaction temperature, or the reaction may be effected with an inert solvent or suspension agent which is still liquid at the reaction temperature, such as hexane.

The reactions in accordance with process (a) or (b) yield a mixture of compounds of formula I wherein R is in a trans position to the hydrogen atom in the $C_3$ position (epivincanol derivatives) and compounds of formula I wherein R is in a cis position to the hydrogen atom in the $C_3$ position (vincanol derivatives). These compounds may be separated in accordance with known methods, e.g., by fractional crystallization or chromatography.

The compounds of formula I obtained in accordance with the process of the invention may exist in free base form, or in acid addition salt forms. Acid addition salt forms, e.g. the hydrogen fumarate or the p-toluene sulphonate, may be produced from the free base forms in conventional manner and vice versa.

The starting materials are known or may be produced in accordance with known methods.

In the following non-limitative Examples all temperatures are indicated in degrees Centigrade.

It will be appreciated that where one isomer is separated off, the other isomer at position 14 may also be obtained from the residual portion in conventional manner.

EXAMPLE 1

14-Deoxy-14-(2-hydroxyethylthio)vincanol [process a)]

13.92 g (50 millimols) of (3S,16S)-eburnamenine and 4.69 g (60 millimols) of mercaptoethanol are dissolved in 60 cc of a 1 molar solution of methanesulphonic acid in chloroform, and the solution is allowed to stand at 20° for 2 hours. After distributing between 50 cc of 2 N aqueous ammonia and methylene chloride, drying and concentrating by evaporation, a resinous residue is obtained. Crystallization from 2-propanol at 0° yields the title compound having a M.P. of 175°.

EXAMPLE 2

O-methyl-vincanol and O-methyl-epivincanol 27.84 g (100 millimols) of (3S,16S)-eburnamenine are dissolved in 100 cc of 1 molar absolute methanolic sulphuric acid and the solution is boiled for 30 minutes under nitrogen. After distributing between 200 cc of 2N ammonia and methylene chloride, drying and concentrating by evaporation, an amorphous material consisting of a mixture of the two epimeric bases, is obtained. Fractional crystallization of the hydrogen fumarates from 2-propanol at 0°, first yields crystals of O-methyl-vincanol hydrogen fumarate, M.P. 161° (decomp.), and then crystals of O-methyl-epivincanol hydrogen fumarate, M.P. 110° (decomp.).

The bases are liberated by distributing between 2 N aqueous ammonia and methylene chloride. Crystallization of the resulting oily residues from 2-propanol yields O-methyl-vincanol, having a M.P. of 106°, or O-methyl-epivincanol, having a M.P. of 163°.

EXAMPLE 3

14-Deoxy-14-methylthio-vincanol [process b)]

a. Production of the hydrogen halide addition product of (3S,16S)-eburnamenine

Absolute hydrogen bromide gas is passed through 27.84 g of (3S,16S)-eburnamenine at −78°, while stirring, and condensation is effected until a clear yellow solution is formed at a volume of 100 cc. While the solution is still in the dry ice bath, concentration is effected at a vacuum of 200 mm of Hg, while stirring, until a mash which solidifies is obtained, and the residue is subsequently dried at −78° and 20 mm of Hg without stirring for 16 hours. After filling the vacuum with nitrogen, the brittle residue is pulverized at −78°.

b) 14-Deoxy-14-methylthio-vincanol 100 cc of methanethiol are added to the pulverized residue at −78°, while stirring, the mixture is allowed to warm to 0° while stirring for one hour, and is stirred for a further hour at 0°. The reaction mixture is then distributed between 500 cc of 2 N ammonia and 200 cc of methylene chloride, the methylene chloride solution is concentrated by evaporation and the title compound is crystallized from methanol. M.P. 199°.

The following compounds of formula Ia may also be obtained in a manner analogous to Example 1, using the corresponding compounds of formulae II and III:

| | Compounds of formula Ia | | |
|---|---|---|---|
| Example | R' | X | M.P. |
| 4 | ---SCH (CH$_3$)$_2$ | H | 95° |
| 5 | ---S(CH$_2$)$_3$CH$_3$ | H | of the p-toluene-sulphonate: 167° |
| 6 | ---SCH$_3$ | H | 199° |
| 7 | ---SCH$_3$ | 10-F | 155° |

The following compounds of formula I may be obtained in a manner analogous to Example 3, using the corresponding starting materials of formula IV wherein Z is bromine:

| | Compounds of formula I | | | using compounds of |
|---|---|---|---|---|
| Ex. | R | X | M.P. | formula V |
| 8 | ---N(CH$_3$)$_2$ | H | 134° | HN(CH$_3$)$_2$ |
| 9 | ---S(CH$_2$)$_2$OH | H | 175° | HS(CH$_2$)$_2$OH |
| 10 | ---OCH$_3$ | H | 106° | NaOCH$_3$ |
|  | ◂OCH$_3$ | H | 163° |  |
| 11 | ---SCH(CH$_3$)$_2$ | H | 95° | HSCH(CH$_3$)$_2$ |
| 12 | ---S(CH$_2$)$_3$CH$_3$ | H | of the p-toluene-sulphonate: 167° | HS(CH$_2$)$_3$CH$_3$ |
| 13 | ◂O(CH$_2$)$_3$CH$_3$ | H | 84° | NaO(CH$_2$)$_3$CH$_3$ |
| 14 | ---SCH$_3$ | 10-F | 155° | HSCH$_3$ |
| 15 | ◂NH$_2$ | H | 123° | NH$_3$ |

In analogous manner to that described in Example 3, there are obtained the following compounds of formula I wherein

| X | R |
|---|---|
| 10-Br | ----O . CH$_2$ . CH$_2$ . CH$_2$ . NH$_2$ |

| -continued | |
|---|---|
| X | R |
| 11-Br | ----SCH$_3$ |
| 10-Cl | ----S . CH$_2$ . CH$_2$ . CH$_2$ . NH$_2$ |
| 11-Cl | ----O . C$_6$H$_5$ |
| H | ----S . C$_6$H$_5$ |
| H | ----O . [CH$_2$]$_4$ . C$_6$H$_5$ |
| H | ----S . [CH$_2$]$_4$ . C$_6$H$_5$ |
| H | ----NH$_2$ |
| H | ----N(C$_6$H$_5$) . CH$_2$ . C$_6$H$_5$ |

The compounds of formula I are useful because they possess pharmacological activity in animals. In particular the compounds are useful as psychostimulants for stimulating the central nervous system as indicated in standard tests. For example in one standard test the compounds are administered s.c. to mice. The increase in excitability in the mice is then observed over a period of e.g., 2 hours. In general the compounds are administered at a dosage of from about 10 to about 100mg/kg animal body weight.

The compounds are additionally useful as vigilance-increasing agents useful in the treatment of, for example, cerebral insufficiency, e.g., for the treatment of cerebral vascular damages, cerebral sclerosis, or loss of consciousness due to skull traumas, as indicated in standard tests. For example in one test following the method described in Depoortere H. and Loew D. in the Nature of Sleep, Int. Symp. pp. 101–104 (1973) Fischer, Stuttgart; and Depoortere H. First European Congress on Sleep Research, Basel, 1972, pp. 360–365, Karger, Basel (1973) the compounds are administered to rats having electrodes chronically planted in the brain. The increase of the wake phase and the decrease in paradoxical and classical sleep phases are determined in conventional manner using the electroencephalograph. In general the compounds are administered at a dosage of from about 10 to about 30 mg/kg animal body weight.

For the above mentioned uses the dosage will, of course, vary depending on the compound employed, mode of administration and therapy desired. However, in general, satisfactory results are obtained when administered at a daily dosage of from 0.01 mg to about 100 mg per kg animal body weight, conveniently given in divided doses 2 to 4 times a day or in sustained release form. For the larger mammal, the total daily dosage is in the range from about 1 to about 500 mg, and dosage forms suitable for oral administration comprise from about 0.25 mg to about 250 mg, e.g., 0.5 to 30 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be formulated in conventional manner so as to be, for example, a solution or a tablet.

Suitable acids for salt formation include hydrochloric acid, sulphuric acid, malonic acid, maleic acid, and methane sulphonic acid.

The compounds of Examples 1 and 3 exhibit particularly interesting activity.

In one group of compounds X is hydrogen. In a sub-group R is alkoxy, alkylthio or dialkylamino. In another sub-group R is methoxy, iso-propylthio, n-butylthio or 2-hydroxyethylthio.

In one group of compounds X is in the 10-position.

In another group of compounds R is NR$_3$R$_4$, wherein R$_3$ is alkyl, phenyl or phenylalkyl and R$_4$ is as defined above.

I claim:

1. A compound of formula I,

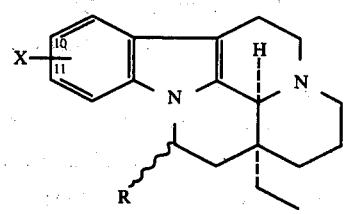

wherein
X is hydrogen or halogen having an atomic number from 9 to 35 in the 10- or 11-position, and
R is NR$_3$R$_4$, and
R$_3$ and R$_4$ are, independently, hydrogen, alkyl or 1 to 4 carbon atoms, phenyl or phenylalkyl of 7 to 10 carbon atoms in the aggregate thereof,
or a pharmaceutically acceptable acid addition salt thereof.

2. A compound of claim 1, wherein X is hydrogen.

3. The compound of claim 2 wherein R is dialkylamino.

4. A compound of claim 1, wherein R is trans to the hydrogen atom at C-3.

5. A compound of claim 1, wherein R is cis to the hydrogen atom at C-3.

6. The compound of claim 1 wherein R and X are --N(CH$_3$)$_2$ and H, respectively.

7. The compound of claim 1 wherein R and X are --NH$_2$ and H, respectively.

8. A compound of formula

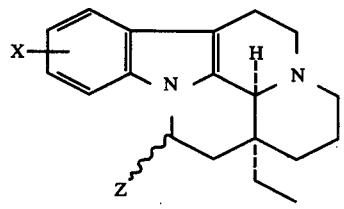

wherein
X is as defined in claim 1, and
Z is chloro or bromo.

9. A vigilance increasing composition comprising an effective vigilance increasing amount of a compound of the formula

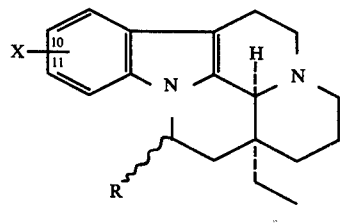

wherein

X is hydrogen or halogen having an atomic number from 9 to 35 in the 10- or 11-position, and R is $SR_2$ or $NR_3R_4$, wherein $R_2$ is alkyl of 1 to 4 carbon atoms, hydroxyalkyl or aminoalkyl of 2 to 4 carbon atoms, wherein the hydroxy and amino groups are in other than the α-position to the O or S atom, phenyl or phenylalkyl of 7 to 10 carbon atoms in the aggregate thereof, and $R_3$ and $R_4$ are, independently, hydrogen, alkyl or 1 to 4 carbon atoms, phenyl or phenylalkyl of 7 to 10 carbon atoms in the aggregate thereof, or a pharmaceutically acceptable acid addition salt thereof in association with a pharmaceutical carrier or diluent.

10. A method of increasing vigilance in animals, which comprises administering to an animal in need of such treatment a effective vigilance increasing amount of a compound of the formula

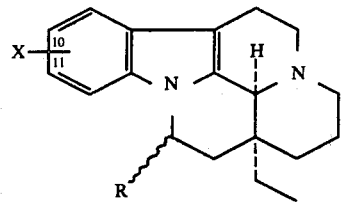

where X and R are as defined in claim 9.

11. A method of psychostimulation in animals, which comprises administering to an animal in need of such treatment an effective psychostimulating amount of a compound of the formula

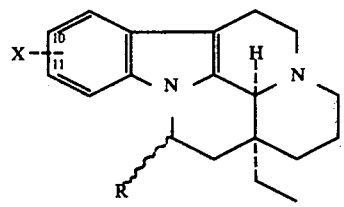

where X and R are as defined in claim 9.

* * * * *